United States Patent [19]

Carver, Jr. et al.

[11] Patent Number: 5,187,673
[45] Date of Patent: Feb. 16, 1993

[54] METHOD AND APPARATUS FOR DETERMINING THE DISTRIBUTION OF CONSTITUENT SUBPOPULATIONS WITHIN A POPULATION OF PARTICLES HAVING OVERLAPPING SUBPOPULATIONS

[75] Inventors: Edward L. Carver, Jr., 18 Lisa Dr., Oxford, Conn. 06483; Richard D. DeVeaux, Princeton, N.J.; David C. DeCava, Oxford, Conn.

[73] Assignee: Edward L. Carver, Jr., Oxford, Conn.

[21] Appl. No.: 651,686

[22] Filed: Feb. 5, 1991

[51] Int. Cl.$^5$ .................... G06F 15/36; G06F 15/42; G01N 15/02
[52] U.S. Cl. ................................. 364/555; 364/554; 364/413.07; 324/71.4
[58] Field of Search ............... 364/555, 554, 413.07, 364/551.01; 324/71.4; 436/63; 356/39, 40, 335

[56] References Cited

U.S. PATENT DOCUMENTS

| | | | |
|---|---|---|---|
| 4,314,346 | 2/1982 | Feier et al. | 364/413.07 |
| 4,375,615 | 6/1980 | Haynes | 324/71.4 |
| 4,488,248 | 12/1982 | Okada et al. | 364/555 |
| 4,491,926 | 3/1982 | Okada et al. | 364/555 |
| 4,706,207 | 6/1985 | Hennessy et al. | 364/555 |
| 4,710,021 | 10/1986 | von Behrens | 356/72 |
| 4,801,549 | 9/1987 | Cremins et al. | 436/63 |
| 4,817,446 | 4/1989 | Kanamori | 364/555 |
| 4,933,884 | 6/1990 | Lorenz | 364/413.07 |
| 5,059,395 | 10/1991 | Brittenham et al. | 356/335 |

OTHER PUBLICATIONS

DeVeaux, R. D. et al., "Robust Estimation of a Normal Mixture", Statistics and Probability Letters, vol. 10, pp. 1-7, Jun. 1990.
Dempster, A. P. et al., "Maximum Likelihood From Incomplete Data via the EM Algorithm", Journal of Royal Statistical Society, Series B, vol. 39, pp. 1-38 (1977) Jan.
DeVeaux, R., "Mixtures of Linear Regressions", Computational Statistics & Data Analysis, vol. 8, pp. 228-245 (1989).
Izenman, A. J., "Philatelic Mixtures and Multiple Densities", Journal of the American Statistical Association, vol. 83, No. 404, Dec. (1988).
Woodward, W. A., "A Comparison of Minimum Distance and Maximum Likelihood Estimation of a Mixture Proportion", Journal of the American Statistical Assoc., vol. 79, No. 387, pp. 590-598 (1984) Sep.
Rowan, R. M., "Blood Cell Volume Analysis", (1983) Albert Clark & Co. Ltd., London, England.
England, J. M., "Advances on Hematological Methods: the Blood Count" (1982) CRC Press Inc., Boca Raton, Fla.
Segal, A. W. et al., "Rapid Single Centrifugation Step Method for the Separation of Erythrocytes, Granulocytes, and Mononuclear Cells on Continuous Density Gradients of Percoll", Journal of Immunological Methods, vol. 32, pp. 209 214 (1980), Jan.
Pertoft, H., "Cell Separation Methods and Selected Application, Sedimention of Cells in Colloidal Silica (Percoll)", vol. 1, pp. 115-152 (1982).
DeVeaux, R. D., "Parameter Estimation for a Mixture of Linear Regressions", Ph.D. Dissertation published in Technical Report No. 247 (Apr., 1986) Department of Statistics, Stanford University, Palo Alto, Calif.

(List continued on next page.)

Primary Examiner—Parshotam S. Lall
Assistant Examiner—Michael Zanelli
Attorney, Agent, or Firm—Kramer, Brufsky & Cifelli

[57] ABSTRACT

A method and appartatus for determining the parameters (i.e., proportion, mean, and standard deviation) of constituent subpopulations within a sample population of particles which contains overlapping populations. The invention includes the use of the EM algorithm, an iterative process which estimates the probability that a particle belongs to any given overlapping subpopulation.

13 Claims, 2 Drawing Sheets

OTHER PUBLICATIONS

"ICSH Recommendations for the Analysis of Red Cell, White Cell and Platelet Size Distribution Curves: I General Principles", J. Clin. Pathol., vol. 35, pp. 1320–1322, 1982, May.

McLaren, C. E. et al., "Analysis of the Volume of Red Blood Cells: Application of the Expectation–Maximization Algorithm to Grouped Data from the Doubly--Truncated Lognormal Distribution", Biometrics, vol. 42, pp. 143–158, 1986, Mar.

McLaren, C. E. et al., "Statistical and Graphical Evaluation of Erythrocyte and Volume Distributions", Am. J. Physiol., vol. 252, pp. H857–H866, 1987, Mar.

"ICSH Recommendations for the Analysis of Red Cell, White Cell and Platelet Size Distribution Curves, Method for Fitting a Single Reference Distribution and Assessing Its Goodness of Fit." Clin. Lab. Haema., vol. 12, pp. 417–431, 1990, Mar.

METHOD AND APPARATUS FOR DETERMINING THE DISTRIBUTION OF CONSTITUENT SUBPOPULATIONS WITHIN A POPULATION OF PARTICLES HAVING OVERLAPPING SUBPOPULATIONS

BACKGROUND OF THE INVENTION

The present invention relates to a method and apparatus for determining the distribution of constituent subpopulations within a population of particles having overlapping subpopulations.

In both industry and science, it is frequently necessary that information be obtained regarding the distribution of constituent subpopulations within a diverse population of particles. For example, in the field of medicine, it is possible to detect abnormalities in a patient's blood by measuring the distribution of various subpopulations of white blood cell species that are present therein. Typically, such information is obtained using a particle distribution analyzer, such as the one described in U.S. Pat. No. 4,491,926 to Okada et al., which is specifically incorporated herein by reference.

Such analyzers typically include a detector which is adapted to detect particles by electrical or optical differences from a medium containing the particles in dispersion and to generate signals proportional to the differences, a parameter extraction circuit which is adapted to measure the signal corresponding to each particle, an analog to digital converter for converting the measured signal into digital form for processing, and a memory for storing the information corresponding to each particle. Optionally, the analyzer may further include a histogrammer, which is used to process the information into the form of a histogram. Histograms are graphic representations of frequency distributions in which the widths of contiguous vertical bars are proportional to the class widths for a selected property and the heights of the bars are proportional to the class frequencies. By comparing the histogram obtained for the sample to a reference histogram, one may draw a conclusion regarding the normalcy of the sample.

Unfortunately, in many situations, two or more of the subpopulations within the sample possess overlapping ranges with respect to the property being measured. For example, in the case of white blood cells, the size ranges for the various varieties overlap considerably (e.g., variety 1 ranges in size from 100 femtoliters to 325 femtoliters; variety 2 ranges in size from 75 femtoliters to 125 femtoliters; etc.). Because of this overlap, a histogram will, to a lesser or greater extent, merge the representations of the subpopulations, making it impossible to accurately determine the distribution of or, in some cases, the existence of the constituent subpopulations. These merged subpopulations are frequently referred to in the art as hidden, overlapping, or poorly defined subpopulations.

One approach to this problem has been to resolve the overlapping subpopulations by measuring an additional property which does not result in overlap of the same subpopulations. For example, in the case of white blood cells, opacity and/or density may be measured in addition to size. As can readily be appreciated, this approach suffers from being both time-consuming and costly since the analytical equipment must be capable of making the various types of measurements described above for each particle.

Another approach to this problem has been to resolve the overlapping subpopulations into their constituent subpopulations using mathematical models which truncate the crude data. For example, U.S. Pat. No. 4,706,207 to Hennessy et al., which is specifically incorporated herein by reference, describes a method which involves counting the number of objects in a particular "channel" (a very limited band of objects), making similar counts in adjacent channels, employing cutoff points made at selected ends of the normal curve within regions where other objects are not usually detected, and then extrapolating the rest of the curve based on the typical shape of known object distribution curves. The shortcomings of this method are that not all the raw data are used in the analysis and that, in the normal situation, points obtained in the log versus delta log plot will not fall strictly along a straight line, making it necessary to find a mean value straight line. In addition, in using this technique, criteria about whether certain counts should be taken or discarded have to be developed. Consequently, only a rough estimate of the distribution of the overlapping subpopulations can be determined with this method.

SUMMARY OF THE INVENTION

Accordingly, it is an object of the present invention to provide a method and apparatus for determining accurately the parameters (i.e., proportion, means, and standard deviation) of constituent subpopulations within a sample which contains a population of particles which includes overlapping subpopulations.

It is a feature of the present invention that the raw data of a distribution histogram are processed using the EM algorithm.

It is an advantage of the present invention that all of the raw data may be used in the analysis.

Additional objects, features and advantages of the present invention will be set forth in part in the description which follows, and in part will be obvious from the description or may be learned by practice of the invention. The objects, features and advantages of the invention may be realized and attained by means of the instrumentalities and combinations particularly pointed out in the appended claims.

To achieve the foregoing objects, features and advantages and in accordance with the purpose of the invention, as embodied and broadly described herein, a method for determining the parameters of constituent subpopulations within a sample which contains a population of particles which includes overlapping subpopulations, comprises determining the total number of constituent subpopulations within the population, selecting an equation that describes the distribution of particles within each subpopulation based on a measurable optical or electrical property, measuring each of the particles in the population for the property, and then calculating the parameters for each subpopulation using the EM algorithm.

Additionally, to achieve the foregoing objects, features and advantages and in accordance with the purpose of the invention, as embodied and broadly described herein, an apparatus for determining the parameters for constituent subpopulations within a sample which contains a population of particles which includes overlapping subpopulations, comprises means for generating an electrical signal for each particle in the population wherein the characteristics of the signal are related to an electrical or optical property of the particle, means for amplifying the signals outputted by the signal generating means, means for measuring the characteristics of the amplified signals, means for digitizing the output of the measuring means, and means for processing the digitized information in accordance with the EM algorithm so as to obtain the parameters.

The accompanying drawings, which are hereby incorporated in and constitute a part of this Specification, illustrate the preferred embodiments of the invention and, together with the description, serve to explain the principles of the invention.

DETAILED DESCRIPTION OF A PREFERRED EMBODIMENT

The present invention is directed to a method and apparatus for determining the parameters of constituent subpopulations within a sample which contains a population of particles including overlapping subpopulations.

Figure 1:
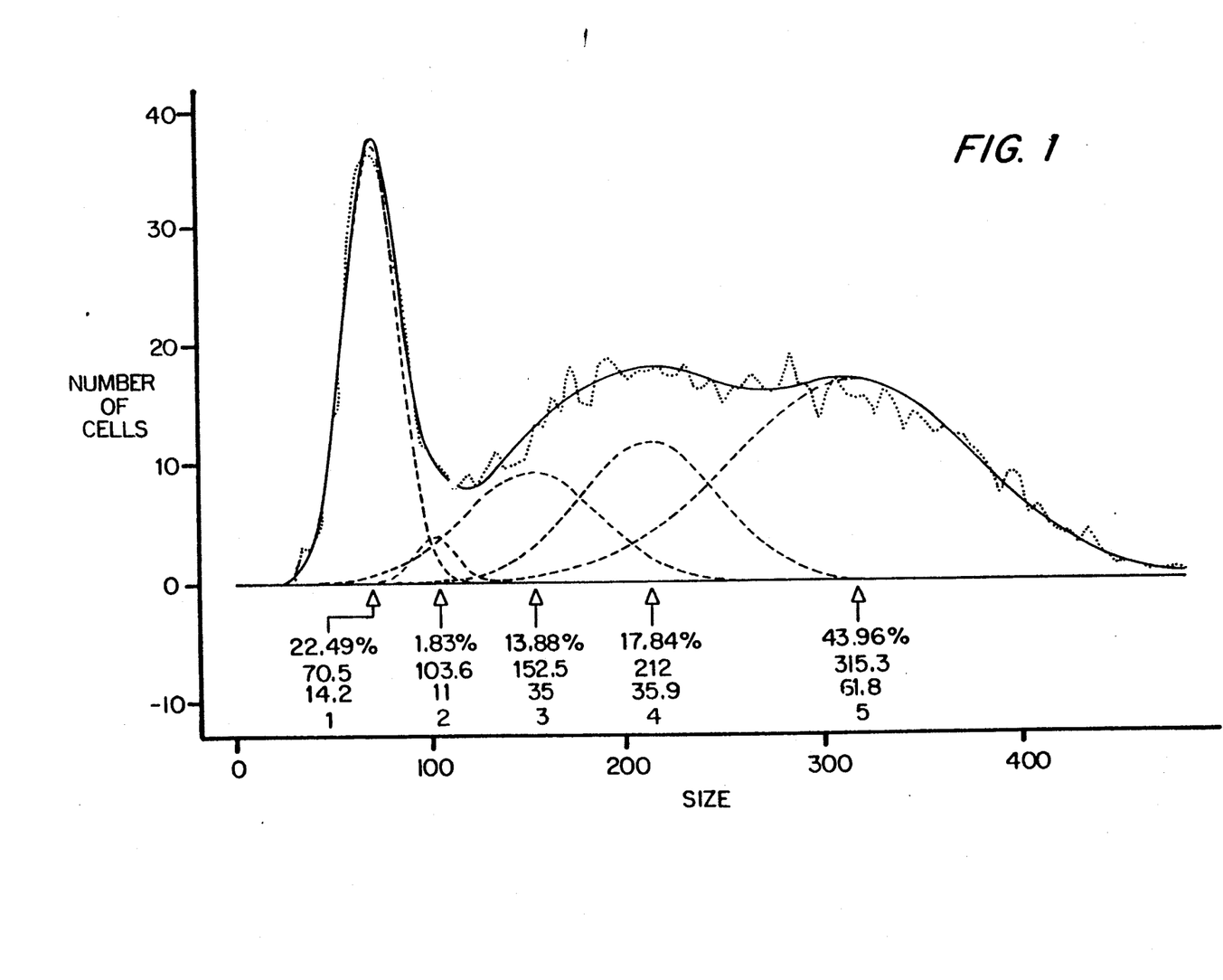
FIG. 1 shows a population of white blood cells which includes overlapping subpopulations and demonstrates the improvement in results obtained by using the method of the present invention.

Referring now to FIG. 1, a particle size histogram of a population of white blood cells present in a sample is represented by the solid line. Based on the histogram, it would appear that there are three subpopulations in the sample, the first subpopulation being represented by the sharp curve extending from about 25 femtoliters to about 100 femtoliters, the second and third subpopulations being represented by the broader curves extending from about 100 femtoliters to about 250 femtoliters and from about 250 femtoliters to about 400 femtoliters, respectively. As noted previously, however, it is known that there are normally five different varieties of white blood cells present. Consequently, one would expect to see five curves in the histogram corresponding to the five different types of cells. The reason why only three curves appear in the histogram is that the five subpopulations of white blood cells do not possess discrete subpopulations with respect to the physical property being measured, namely, particle size. Consequently, the five curves overlap to give the three curves seen.

The method of the present invention corrects this deficiency by including a statistical algorithm which, for example, in FIG. 1 accurately resolves the three curves into the five constituent subpopulations represented by the dotted lines. Preferably, the statistical method of the present invention is the EM algorithm, which is described in R. D. DeVeaux et al., Robust Estimation of a Normal Mixture, Statistics and Probability Letters, Vol. 10, pp. 1-7 (June 1990), A. P. Dempster et al., Maximum Likelihood from Incomplete Data via the EM Algorithm, Journal of Royal Statistical Society, Series B, Vol. 39, pp. 1-38 (1977), R. DeVeaux, Mixtures of Linear Regressions, Computational Statistics & Data Analysis, Vol. 8, pp. 227-245 (1989), A. J. Izenman et al., Philatelic Mixtures and Mutimodal Densities, Journal of the American Statistical Association, Vol. 83, No. 404 (1988), W. A. Woodward et al., A Comparison of Minimum Distance and Maximum Likelihood Estimation of a Mixture Proportion, Journal of the American Statistical Association, Vol. 79, No. 387, pp. 590-598 (1984), all of which are specifically incorporated herein by reference. The present invention, however, is not limited to use of the EM algorithm and is intended to encompass the use of any comparable statistical algorithm which can use, but is not limited to using, all of the raw data from a histogram to resolve overlapping subpopulations. An example of such an alternative algorithm uses the minimum distance approach.

For illustrative purposes only, the method of the present invention will be described in the context of determining the distribution of constituent subpopulations within a sample population of white blood cells. It is to be understood, however, that the method of the present invention is generally applicable to determining the distribution of constituent subpopulations within a sample population of any type of particle, including but not limited to biological cells, glass, latex spheres, pollen, corpuscles, and ceramic particles.

The first step in determining the distribution of constituent subpopulations in a sample population is to determine the number of different subpopulations that exist in the population. In our white blood cell example, this number is five, corresponding to the five different varieties of white blood cells.

The next step is to separately characterize each of the subpopulations based on a physical property, such as size, density, opacity, etc., that can be measured by electrical or optical means. In our white blood cell example, this involved making histograms based on particle size for each of the five subpopulations. From each histogram, an equation is then selected which accurately describes the distribution of particles within the subpopulation. This may be determined empirically by physical separation methods, as described in R. M. Rowan, Blood Cell Volume Analysis-A New Screening Technology for the Haematologist, published by Albert Clark and Company Lim (1990); Advances in Hematological Methods: The Blood Count, edited by J. M. England (1982); A. W. Segal et al., A Rapid Single Centrifugation Step Method for the Separation of Erythrocytes, Granulocytes, and Mononuclear Cells on Continuous Density Gradients of Percoll, Journal of Immunological Methods, Vol. 32, pp. 209-214 (1980); and H. Perotft et al., Sedimentation of Cells in Colloidal Silica (Percoll), Cell Separation Methods and Selected Applications, Vol. 1, pp. 115-152 (1982), all of which are specifically incorporated herein by reference. For the white blood cell subpopulations, all of which were Gaussian (normal) in shape, the equation is as follows:

$$f(x) = \frac{1}{\theta \sqrt{2\pi}} e^{-((x-\mu)^2/2\theta^2)}$$

where $\theta$ = the standard deviation and $\mu$ is the mean of the population.

In order to incorporate the equation into a software program, slight changes have been made. The constants $\pi$ and $e$ are handled separately.

Next, each of the particles in the sample population is measured for the selected property. This is done in the known fashion, such as by using particle analzyers of the type described in U.S. Pat. Nos. 4,706,207, 4,491,926, 4,801,549, 4,710,021, and 4,375,615, all of which are specifically incorporated by reference.

All of the information obtained in the manner described above is then fed into a processor which, using the EM algorithm, determines the distribution of the constituent subpopulations. An example of a computer program which embodies the EM algorithm for this purpose is listed at the end of the Detailed Description (see Appendix A). This program is written in the computer language "C."

An example of the output values from this program for the data shown in FIG. 1 is as follows:

| Population # | Population Proportion $\lambda$ = proportion (%/100) | Population Mean $\mu$ = mean | Population Standard Deviation $\theta = \sqrt{\text{variance}}$ |
|---|---|---|---|
| 1 | 0.2249 | 70.5 | 14.2 |
| 2 | 0.0183 | 103.6 | 11.0 |
| 3 | 0.1388 | 152.5 | 35.0 |
| 4 | 0.1784 | 212.0 | 35.9 |
| 5 | 0.4396 | 315.3 | 61.8 |

Figure 2:
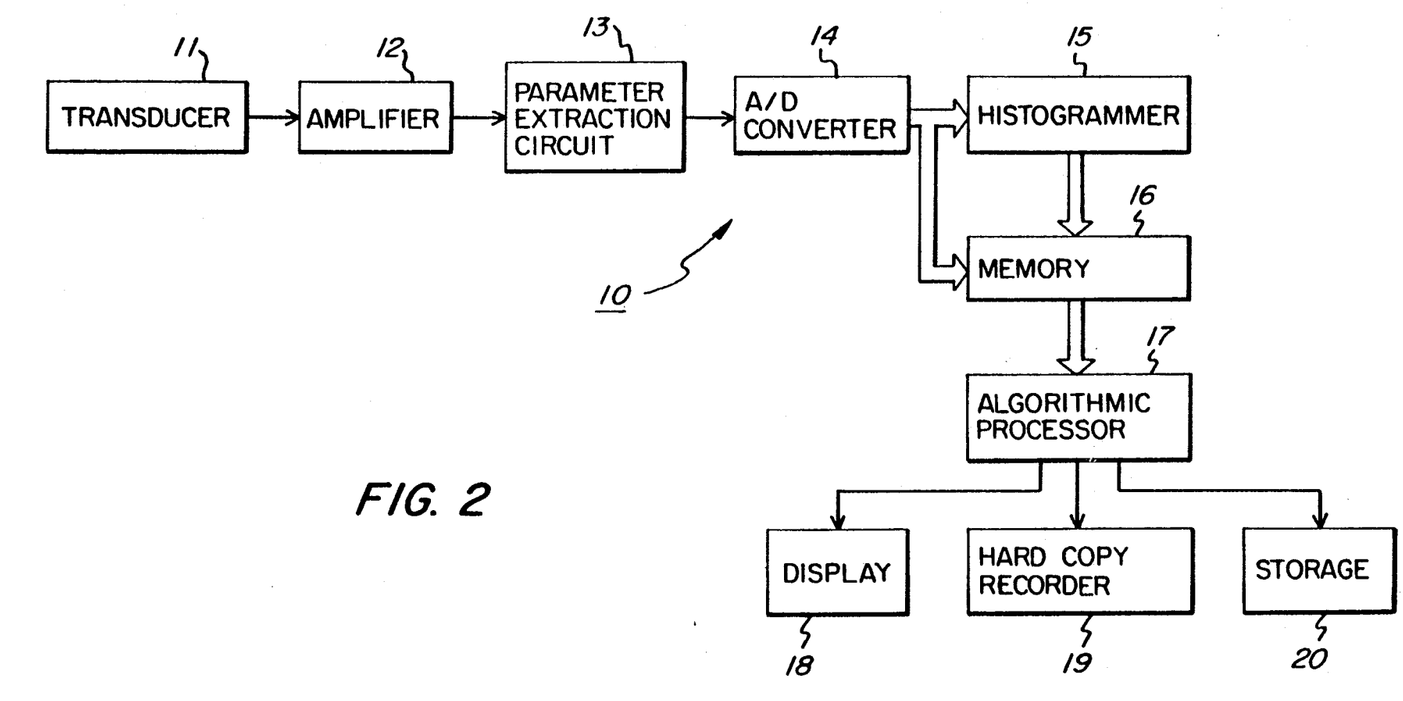
FIG. 2 is a schematic diagram of an apparatus constructed according to the teachings of the present invention.

Referring now to FIG. 2, there is illustrated a schematic representation of an apparatus constructed according to the teachings of the present invention and represented generally by reference numeral (10).

Apparatus (10) includes a transducer (11), which detects differences in electrical, optical, chemical, or other characteristics in each of the particles and then generates a signal whose characteristics relate to such differences. For example, a transducer (11) may be used to generate signals relating to the diameter, volume, optical or physical density or flourescent intensity of each of the particles.

An amplifier (12) receives the signals from the transducer (11) and amplifies them to sufficiently high levels suitable for further processing.

A parameter extraction circuit (13) receives the amplified signals from the amplifier (12) and measures the characteristics of the signal which relate to the property being measured. In a system containing an electrical or optical transducer (11), the measured characteristics may include pulse height, which relates to the volume or internal structure of the objects, or pulse width, which relates to the time of flight or diameter of the particles.

An analog to digital (A/D) converter (14) is used to convert the signals processed by the parameter extraction circuit (13) into a digital form suitable for digital processing. The output of the A/D converter (14) is then stored in a memory device (16), which records the measured property for each particle.

Finally, an algorithmic processor (17) accesses the contents of the memory (16) and calculates the sizes and proportions of the constituent subpopulations using, for example, the computer program set forth below. The results of the algorithmic process are then fed to a visual electronic display (18), a hard copy recorder (19), or a storage device (20).

A histogrammer (15) is connected between the A/D converter (14) and memory (16) to generate a histogram. The advantage of using a histogrammer is a substantial savings in memory space. However, in a multi-parameter system, the process of histogramming destroys the ability to correlate the multiple parameters on an object by object basis.

In still another embodiment of the present invention, the transducer is adapted to generate signals based on two or more independent characteristics of the particle, such as size and opacity. In such an embodiment, the apparatus further includes a corresponding number of parameter extraction circuits, A/D converters, and histogrammers, if histogrammers are included in the apparatus.

Further modifications of the invention herein disclosed will occur to those skilled in the respective arts and all such modifications are deemed to be within the scope of the invention as defined by the appended claims.

APPENDIX A

```
/* Input values should be in start_in
    number of distributions first, then proportion, mean
    and std dev of each distribution */

/* No graphics output version */

/* This version reads in data from data_in in two columns,
    first is binmidpoint, second is frequency */ include <stdio.h>
include <math.h>
#define MAXREPS 10000
#define ERROR 0.0000000001
#define EPS1 .001
#define EPS2 .01
#define EPS3 .01
define PI 3.14159265 int  i,j,      /* Counter and index variable            */
            saves,     /* Counts floating point error evasions  */
```

```
        save2,      /* Counts variance error evasions        */
        diag,
        nbins,
        npts,
        ndists,
        startj,
        freq[1500],
        nn,
        deltamax,
        reps;       /* Counts iterations of EM procedure     */ double  y[2500],
        f[10],nextf[10],
        W[10][2500],
        rfreq[1500],
        lam[10],
        oldlam[10],
        width, range, min, max, left, right, bottom, height,
        maxh,
        x,yy,leftx,
        oldmean[10],
        oldvrnce[10],
        nmr[10],    /* Numerator for E step of procedure     */
        dnm,        /* Denominator for E step                */
        sum,
        sum22,
        s,
        binsize,
        xbar,
        sum1[10],   /* Scratchpad variables for computation of */
        sum2[10],   /* equations 2.5                           */
        sum3[10],
        delta1,delta2,delta3,
        mean[10],   /* New estimates of means after every    */
        vrnce[10],  /* iteration                             */
        xx,next,density,nextd,
        d[10];      /* Scratchpad variables for t3 computations */

FILE *fopen(),*f_in,*f_out;

main()
{
        sum=sum22=0;
        diag=0;
        f_in = fopen("data_in","r");
        f_out=fopen("data_out","a");
        i=0;
        while (fscanf(f_in,"%lf %d",&x ,&nn) != EOF)
                {
                        y[i] = x;
                        freq[i] = nn;
                        ++i;
                }
        nbins=i;
        min=y[0];
        max=y[nbins-1];
    printf("Read %d bins\n",nbins);
```

```
        printf("Min value is %10.4f, max is %10.4f\n",min,max);
        range=max-min;
        left=min-(.10*range);
        right=max+(.10*range);
        binsize=range/nbins;

npts=0.0;
        for (i=0; i<nbins; ++i)
            npts=npts+freq[i];

maxh=(double)freq[0];
        for (i=1; i<nbins; ++i) {
            if (freq[i]>maxh)
                maxh=(double)freq[i];
            }
        printf("Maximum frequency is %10.4f\n",maxh);
        printf("Total number of points is %d\n",npts);

/* Read starting values for EM from file: "start_in" */ f_in = fopen("start_in","r");
        fscanf(f_in,"%d",&i);
        ndists=i;
        for(j=0;j<ndists;++j)
            {
                fscanf(f_in,"%lf",&x);
                oldlam[j] = x;
                fscanf(f_in,"%lf",&x);
                oldmean[j] = x;
                fscanf(f_in,"%lf",&x);
                oldvrnce[j] = x*x;
            } for(i=0;i<nbins;++i)
            { sum=sum+y[i]*freq[i];
            sum22=sum22+y[i]*y[i]*freq[i];
            }
        xbar=sum/npts;
        s=(sum22-(sum*sum/npts))/(npts-1);
        s=sqrt(s);
        printf("Mean is %f\n",xbar);
        printf("Standard deviation is %f\n",s);

deltamax =1;        /* Initialize convergence criterion */
        saves=save2=0;      /* Initialize error counter.        */
        if (diag==1)
            printf("lambda   mean    std \n");

/* The outside for-loop does iterations of the EM algorithm.
   Execution stops either when the stopping criterion is met
``` or when we reach the MAXREPS number of iterations and give
up.                           */

```
    for (reps=1;reps<=MAXREPS && deltamax;reps++) {
    printf("Number of Iterations is %d\n",reps);
    if (reps == 100 || reps == 500 ){
    for (j=0;j<ndists;++j)
        {
        printf("%d %f %f %f %d\n",
        (j+1),lam[j],mean[j],sqrt(vrnce[j]),reps);
        }
    }
    if (reps == 1000 || reps == 1500 || reps == 2000){
    for (j=0;j<ndists;++j)
        {
        printf("%d %f %f %f %d\n",
        (j+1),lam[j],mean[j],sqrt(vrnce[j]),reps);
        }
    }
    if (reps == 2500 || reps == 3000 || reps == 3500){
    for (j=0;j<ndists;++j)
        {
        printf("%d %f %f %f %d\n",
        (j+1),lam[j],mean[j],sqrt(vrnce[j]),reps);
        }
    }
    if (reps == 4000 || reps == 5000 || reps == 6000){
    for (j=0;j<ndists;++j)
        {
        printf("%d %f %f %f %d\n",
        (j+1),lam[j],mean[j],sqrt(vrnce[j]),reps);
        }
    }
    if (reps == 7000 || reps == 8000 || reps == 9000){
    for (j=0;j<ndists;++j)
        {
        printf("%d %f %f %f %d\n",
        (j+1),lam[j],mean[j],sqrt(vrnce[j]),reps);
        }
    }
      for (j=0;j<ndists;++j)
        sum1[j]=sum2[j]=sum3[j]=0.0;
```

/* The inside for-loop performs the computation of equations 2.2,
   2.3 and 2.5 for each observation in the input (y) vector,
   using either a normal or t3 distribution depending on the
   value of the distrib flag.          */

```
    for (i=0;i<nbins;++i) {
      dnm=0;
      for (j=0;j<ndists;++j)
        {
            d[j]= y[i]-oldmean[j];
            nmr[j]= oldlam[j]*exp((-d[j]*d[j])/
                (oldvrnce[j]*2.0))/sqrt(oldvrnce[j]);
            dnm = dnm + nmr[j];
        }
      for (j=0;j<ndists;++j)
        {
```

```
            W[j][i] = nmr[j]/dnm;
          }
        for (j=0;j<ndists;++j)
          {
          sum1[j] += W[j][i] * freq[i];
          sum2[j] += W[j][i]* y[i] * freq[i];
          sum3[j] += W[j][i]* y[i] *y[i] * freq[i];
          }
      }

/* Set new values for the parameters based on Wij */ for (j=0;j<ndists;++j)
          {
          lam[j]=sum1[j]/ npts;     /* Equation 2.5a    */
          mean[j]=sum2[j]/sum1[j];  /* Equation 2.5b    */
          vrnce[j]=(sum3[j]-sum1[j]*mean[j]*mean[j])/sum1[j];
      }

/* If diagnostics flag set, print diagnostics.        */ if(diag==1) {
   for(j=0;j<ndists;++j)
       printf("%d %0.4f  %5.4f  %5.4f\n",
           (j+1),lam[j],mean[j],sqrt(vrnce[j]));
           }

/* Computations to check convergence criterion.  The criterion
   is: If any two means or variances computed on successive
   iterations of the EM procedure differ by less than EPS,
   stop.                         */ delta1=delta2=delta3=0;
   for(j=0;j<ndists;++j)
       {
            delta2 = delta2 + fabs(oldmean[j]-mean[j]);
            delta3= delta3 + fabs(sqrt(oldvrnce[j])-sqrt(vrnce[j]));

delta1 = delta1 + fabs(oldlam[j]-lam[j]);
       }
    if (delta1 < EPS1 && delta2 < EPS2 && delta3 < EPS3)
        deltamax = 0;

/* Assign newly-computed values of means and variances to "old"
   variables for use in next EM iteration.                  */ for (j=0;j<ndists;++j)
       {
                oldmean[j]=mean[j];
            oldvrnce[j]=vrnce[j];
            oldlam[j]=lam[j];
            }

}

/* End iteration */
```

```
if(saves>0)    printf("%d    floating    point    exception(s)
avoided.\n\n",saves);
if (save2>0) printf("%d zero-variance error(s) avoided.\n",save2);
for (j=0;j<ndists;++j)
    {
    printf("%d %f %f %f %d\n",
        (j+1),lam[j],mean[j],sqrt(vrnce[j]),reps);
    }
f_out=fopen("data_out","a");
fprintf(f_out,"Pop Number Lambda     Mean   Std Dev Reps\n");
for (j=0;j<ndists;++j)
    fprintf(f_out,"%6d %10.4f %10.4f %10.4f %4d\n",
        (j+1),lam[j],mean[j],sqrt(vrnce[j]),reps);
fclose(f_out);

}
/* End of mixmean program.                                     */
```

What is claimed is:

1. An apparatus for determining the parameters of constituent subpopulations within a sample which contains a population of particles which includes overlapping subpopulations, said apparatus comprising
   a) means for generating an electrical signal for each particle in the population wherein the characteristics of the signal are related to an electrical or optical property of the particle;
   b) means for amplifying the signals outputted by the signal generating means;
   c) means for measuring the characteristics of the amplified signals,
   d) means for digitizing the output of the measuring means; and
   e) means for processing the digitized information in accordance with the EM algorithm so as to obtain the parameters.

2. The apparatus as claimed in claim 1, further comprising a histogrammer wherein the output of said digitizing means is fed to the input of said histogrammer, the output of said histogrammer being fed to the input of said processing means.

3. An apparatus as defined in claim 1, wherein said means for generating an electrical signal for each particle in the population includes a transducer for detecting characteristics of the particles and generating a signal indicative of at least one characteristic.

4. An apparatus as defined in claim 1, wherein the means for measuring the characteristics of the amplified signals includes a parameter extraction circuit.

5. An apparatus for determining the parameters of constituent subpopulations within a sample containing a population of particles including overlapping subpopulations, comprising:
   an analyzing device for detecting characteristics of the particles and generating signals indicative of at least one characteristic;
   a measuring device for measuring at least one characteristic of the signals from the analyzing device indicative of at least one property of the particles being measured, and for generating signals indicative of the at least one measured characteristic; and
   a processor for employing signals from the measuring device and the EM algorithm to determine the parameters of the constituent subpopulations within the sample.

6. An apparatus as defined in claim 5, further comprising an amplifier for amplifying the signals from the analyzing device prior to transmission of the signals to the measuring device.

7. An apparatus as defined in claim 5, further comprising an analog-to-digital converter for digitizing the signals of the measuring device prior to transmission of the signals to the processor.

8. An apparatus as defined in claim 7, further comprising a memory device for storing the signals digitized by the analog-to-digital converter to record the measured property for the particles, and wherein the processor accesses the contents of the memory device and calculates the sizes and proportions of the constituent subpopulations employing the EM algorithm.

9. An apparatus as defined in claim 5, further comprising a histogrammer coupled between the measuring device and the processor for generating at least one histogram based on the signals from the measuring device.

10. An apparatus as defined in claim 5, wherein the analyzing device includes a transducer for detecting a characteristic of the particles, the characteristic being selected from the group including electrical, optical, and chemical characteristics.

11. An apparatus as defined in claim 10, wherein the transducer generates signals indicative of a characteristic of the particles selected from the group including diameter, volume, optical density, physical density, and fluorescent intensity.

12. An apparatus as defined in claim 5, wherein the measuring device includes a parameter extraction circuit for receiving the amplified signals from the amplifier and for measuring the characteristics of the signals which relate to the property being measured.

13. An apparatus as defined in claim 5, wherein the analyzing device includes a transducer selected from the group including an optical transducer and an electrical transducer, and the at least one characteristic measured by the measuring device is selected from the group including pulse height and pulse width.

* * * * *